United States Patent
Cheng et al.

(10) Patent No.: US 11,969,522 B2
(45) Date of Patent: Apr. 30, 2024

(54) USE OF IMMUNE MODULATORS TO IMPROVE NERVE REGENERATION

(71) Applicants: The Board of Regents of the University of Texas System, Austin, TX (US); Edward Keefer, Dallas, TX (US)

(72) Inventors: Jonathan Cheng, Dallas, TX (US); Edward Keefer, Dallas, TX (US); Srikanth Vasudevan, Dallas, TX (US)

(73) Assignees: The Board of Regents of the University of Texas System, Austin, TX (US); Edward Keefer, Dallas, TX (US)

( * ) Notice: Subject to any disclaimer, the term of this patent is extended or adjusted under 35 U.S.C. 154(b) by 268 days.

(21) Appl. No.: 16/922,355

(22) Filed: Jul. 7, 2020

(65) Prior Publication Data
US 2021/0023264 A1    Jan. 28, 2021

Related U.S. Application Data

(60) Provisional application No. 62/871,552, filed on Jul. 8, 2019.

(51) Int. Cl.
| | | |
|---|---|---|
| A61L 27/18 | (2006.01) | |
| A61K 38/18 | (2006.01) | |
| A61K 45/06 | (2006.01) | |
| A61K 31/395 | (2006.01) | |
| A61K 31/5377 | (2006.01) | |
| C07D 257/02 | (2006.01) | |

(52) U.S. Cl.
CPC .......... *A61L 27/18* (2013.01); *A61K 38/18* (2013.01); *A61K 38/185* (2013.01); *A61K 38/1866* (2013.01); *A61K 45/06* (2013.01); *A61K 31/395* (2013.01); *A61K 31/5377* (2013.01); *A61L 2430/32* (2013.01); *C07D 257/02* (2013.01)

(58) Field of Classification Search
CPC ..... A61L 27/18; A61L 2430/32; A61K 38/18; A61K 38/185; A61K 38/1866; A61K 45/06; A61K 31/395; A61K 31/5377; C07D 257/02
USPC ....................................................... 548/183
See application file for complete search history.

(56) References Cited

U.S. PATENT DOCUMENTS

| | | |
|---|---|---|
| 6,268,352 B1 | 7/2001 | Song et al. |
| 2010/0112038 A1 | 5/2010 | Ruediger et al. |
| 2011/0124706 A1 | 5/2011 | He et al. |
| 2015/0224345 A1 | 8/2015 | Warlick |
| 2016/0031937 A1 | 2/2016 | Sieg |
| 2016/0206592 A1 | 7/2016 | Solomon et al. |
| 2017/0112871 A1 | 4/2017 | Nelson et al. |
| 2017/0224776 A1 | 8/2017 | Chiu et al. |
| 2018/0200232 A1 | 7/2018 | Sun |
| 2018/0296551 A1 | 10/2018 | Solomon et al. |

FOREIGN PATENT DOCUMENTS

| | | |
|---|---|---|
| WO | WO 2008/156644 | 12/2008 |
| WO | WO 2014/137229 | 9/2014 |
| WO | WO 2016/023130 | 2/2016 |

OTHER PUBLICATIONS

Damodaran et al., Nitric Oxide Donors Novel Biomedical Applications and Perspectives, Chapter 6—Nitric Oxide Donors in New Regeneration, 2017, Elsevier Inc., 141-168 (Year: 2017).*
Andereggen et al., "Inflammation and Optic Nerve Regeneration," In: Neuroinflammation: New Insights into Beneficial and Detrimental Functions, Wiley; Hoboken, NJ, 189-204, 2015.
Belmadani et al., "Chemokines regulate the migration of neural progenitors to sites of neuroinflammation," *Journal of Neuroscience*, 2006;26(12):3182-3191.
Bi et al., "Catalpol attenuates nitric oxide increase via ERK signaling pathways induced by rotenone in mesencephalic neurons," *Neurochemistry International*, 2009;54(3-4):264-270.
Bollaerts et al., "Neuroinflammation as Fuel for Axonal Regeneration in the Injured Vertebrate Central Nervous System. Mediators of Inflammation," *Mediators Inflamm.*, 2017;9478542, 2017.
Cui et al., "Nitric oxide donor up-regulation of SDF1/CXCR4 and Ang1/Tie2 promotes neuroblast cell migration after stroke," *J. Neurosci Res.*, 87(1):86-95, 2009.
Dubový, "Spatio-temporal changes of SDF1 and its CXCR4 receptor in the dorsal root ganglia following unilateral sciatic nerve injury as a model of neuropathic pain," *Histochemistry and Cell Biology*, 2010;133(3):323-337.
Dziennis et al., "Role of signal transducer and activator of transcription 3 in neuronal survival and regeneration," *Rev Neurosci.*, 19(4-5):341-361, 2008.
Hilla et al., "CXCR4/CXCL12-mediated entrapment of axons at the injury site compromises optic nerve regeneration," 118(21):e2016409118, 2021.
Hirota et al., "Accelerated Nerve Regeneration in Mice by upregulated expression of interleukin (IL) 6 and IL-6 receptor after trauma," *J. Exp. Med.*, 183:2627-2634, 1996.
Imitola et al., "Directed migration of neural stem cells to sites of CNS injury by the stromal cell-derived factor 1α/CXC chemokine receptor 4 pathway," *Proc Natl Acad Sci USA*, 2004;101(52):18117-18122.
Itoh et al., "The relationship between SDF-1 a / CXCR4 and neural stem cells appearing in damaged area after traumatic brain injury in rats," *Neurol Res.*2009;31(1):90-102.
Keilhoff et al., "Differences in peripheral nerve degeneration/ regeneration between wild-type and neuronal nitric oxide synthase knockout mice," *Journal of Neuroscience Research*, 68:432-441, 2002.

(Continued)

*Primary Examiner* — Kristin A Vajda
(74) *Attorney, Agent, or Firm* — Parker Highlander PLLC

(57) ABSTRACT

The present disclosure describes the use of immune modulators to promote nerve growth and regeneration, particularly in the context of nerve deficit stemming from trauma and disease. In particular, the disclosure provides for the use of CXCR4 antagonsists, STAT3 activators, and an agent that increase nitric oxide, alone or in combination, to treat nerve deficit conditions.

21 Claims, No Drawings

(56) References Cited

OTHER PUBLICATIONS

Küry et al., "Cyclic AMP and tumor necrosis factor-α regulate CXCR4 gene expression in Schwann cells," *Molecular and Cellular Neuroscience*. 2003;24(1):1-9.

Küry et al., "Mammalian achaete scute homolog 2 is expressed in the adult sciatic nerve and regulates the expression of Krox24, Mob-1, CXCR4, and p57kip2 in Schwann cells," *Journal of Neuroscience*, 22(17):7586-7595, 2002.

Leibinger et al., "Neuronal STAT3 activation is essential for CNTF- and inflammatory stimulation-induced CNS axon regeneration," *Cell Death and Disease*, 2013;4(9):e805.

Leibinger et al., "Transneuronal delivery of hyper-interleukin-6 enables functional recovery after severe spinal cord injury in mice," *Nature Communications*, 12:391, 2021.

Li et al., "Chemokine receptor CXCR4 signaling modulates the growth factor-induced cell cycle of self-renewing and multipotent neural progenitor cells," *Glia*, 2011;59(1):108-118.

Liu et al., "AMD3100 inhibits the migration and differentiation of neural stem cells after spinal cord injury," *Scientific Reports*, 7:64, 2017.

Lu et al., "Abnormal development of the hippocampal dentate gyrus in mice lacking the CXCR4 chemokine receptor," *Proc Natl Acad Sci U S A*, 2002;99(10):7090-7095.

McDonald et al., "Regenerative arrest of inflamed peripheral nerves: Role of nitric oxide," *NeuroReport*, 2007;18(16):1635-1640.

Mo et al., "CXCR4/CXCL12 mediate autocrine cell-cycle progression in NF1-associated malignant peripheral nerve sheath tumors," *Cell*, 152(5):1077-1090, 2013.

Negro et al., "An Agonist of the CXCR4 Receptor Strongly Promotes Regeneration of Degenerated Motor Axon Terminals," *Cells*, 8(10):1183, 2019.

Pang et al., "Evaluation of inducible nitric oxide synthase in glaucomatous optic neuropathy and pressure-induced optic nerve damage," *Investigative Ophthalmology and Visual Science*, 2005;46(4):1313-1321.

PCT International Preliminary Report on Patentability issued in International Application No. PCT/US2020/040960, mailed Jan. 20, 2022.

PCT International Search Report and Written Opinion issued in International Application No. PCT/US2020/040960, mailed Oct. 5, 2020.

Ratajczak et al., "Stem cell plasticity revisited: CXCR4-positive cells expressing mRNA for early muscle, liver and neural cells "hide out" in the bone marrow," *Leukemia*, 2004;18(1):29-40.

Sheu et al., "Differential patterns of ERK and STAT3 phosphorylation after sciatic nerve transection in the rat," *Experimental Neurology*, 2000;166(2):392-402.

Stazi et al., "An agonist of the CXCR4 receptor accelerates the recovery from the peripheral neuroparalysis induced by Taipan snake envenomation," *PLoS Negl Trop Dis.*, 14(9):e0008547, 2020.

Stoll et al., Degeneration and regeneration of the peripheral nervous system: From Augustus Waller's observations to neuroinflammation. *Journal of the Peripheral Nervous System*, 2002;7(1):13-27.

Vasudevan, "Long gap peripheral nerve reconstruction using decellularized nerve grafts," The University of Texas at Arlington, 2013.

Wang et al., "SDF-1alpha/CXCR4-mediated migration of systemically transplanted bone marrow stromal cells towards ischemic brain lesion in a rat model," *Brain Res.*, 2008;1195:104-112.

Xu et al., "Chemokine receptor CXCR4 activates the RhoA/ROCK2 pathway in spinal neurons that induces bone cancer pain," *Molecular Pain*, 2020;16.

Yamauchi et al., "Activation of JAK/STAT signalling in neurons following spinal cord injury in mice," *Journal of Neurochemistry*, 2006;96(4):1060-1070.

Zanetti et al., "A CXCR4 receptor agonist strongly stimulates axonal regeneration after damage," *Ann Clin Transl Neurol.*, 6(12);2395-2402, 2019.

Partial Supplementary European Search Report issued in European Application No. 20837543.6, mailed Feb. 14, 2023.

Leibinger et al., "Interleukin-6 contributes to CNS axon regeneration upon inflammatory stimulation," *Cell Death and Disease*, 4:e609, 2013.

Office Action mailed in Chinese Application No. 202080049711.1, mailed Apr. 26, 2023, and English translation thereof.

Scott et al., "Neural regeneration and neuronal migration following injury," *Experimental Neurology*, 131:23-38, 1995.

Extended European Search Report issued in European Application No. 20837543.6, mailed May 16, 2023.

Mehta et al., "Hyperactivated Stat3 boosts axon regeneration in the CNS," *Experimental Neurology*, 280:115-120, 2016.

Watanabe et al., "Axonal regeneration of cat retinal ganglion cells is promoted by nipradilol, an anti-glaucoma drug," *Neuroscience*, 140(2):517-528, 2006.

\* cited by examiner

USE OF IMMUNE MODULATORS TO IMPROVE NERVE REGENERATION

PRIORITY CLAIM

This application claims benefit of priority to U.S. Provisional Application Ser. No. 62/871,552, filed Jul. 8, 2019, the entire contents of which are hereby incorporated by reference.

BACKGROUND

1. Field

The present disclosure relates generally to the fields of medicine and neurobiology. More particularly, it concerns compositions and methods for the treatment of nerve deficits and nerve damage. Specifically, it relates to the use of CXCR4 antagonists, STAT3 activators, and nitric oxide increasing agents, alone or in combination, to treat these conditions.

2. Description of Related Art

Peripheral nerve injuries that require surgical intervention account for ~550,000 patients each year in the United States alone (published by Magellan Medical Technology Consultants, Inc., MN). This enormous clinical need drives peripheral nerve regeneration research (Yannas et al., 2007). The PNS has an inherent capacity to regenerate to a certain extent when subjected to injury. Several commercially available products provide nerve regeneration using exogenous materials to bridge short nerve defects <2-3 cm in length. To date, no widely accepted clinical solutions have: surpassed the "long gap" barrier for manufactured constructs to bridge nerve gaps longer than 2-3 cm in length; increased the rate of nerve regeneration; or increased the quality of nerve regeneration. As such, finding new methods of treating nerve injury that can satisfy these high standards will greatly enhance the ability to treat patients suffering from this common and devastating family of conditions.

SUMMARY

Thus, in accordance with the present disclosure, there is provided a method of enhancing nerve growth, regrowth or regeneration in a subject comprising administering to said subject a CXCR4 antagonist, a STAT3 activator, and/or an agent that increases nitric oxide content. The method may result in bridging of a critical gap of at least 3 cm, such as 3 cm, 3.5 cm, 4 cm, 4.5 cm or 5 cm. Administering may comprise administering a CXCR4 antagonist alone, administering a CXCR4 antagonist with a STAT3 activator, administering a CXCR4 antagonist with an agent that increases nitric oxide content, or administering a CXCR4 antagonist with a STAT3 activator and an agent that increases nitric oxide content.

The method may further comprise inserting a physical support structure into the critical gap, such as a structure composed of poly-lactide acid, polyurethane, polydioxanone, silicone, cellulose, collagen, PLGA, polycaprolactone or processed natural extracellular matrix. The method may further comprise administering to said subject one or more nerve growth factors, such as a neurotrophic (NGF, BDNG, NT-3), a glial-derived (GDNF) and/or a pleotropic (PTN, VEGF) nerve growth factor. The CXCR4 antagonist, said STAT3 activator, said agent that increases nitric oxide content and/or said one or more nerve growth factors may be delivered in a time-dependent release fashion.

In one embodiment, no physical support structure is inserted into said subject, and/or no growth factor is administered to said subject. In another embodiment, the CXCR4 antagonist is administered prior to both the STAT3 activator and the nitric oxide-increasing agent. In yet another rembodiment, the CXCR4 antagonist is administered after both the STAT3 activator and the nitric oxide-increasing agent. In still yet another embodiment, the CXCR4 antagonist may be administered between the STAT3 activator and the nitric oxide-increasing agent.

The subject may suffer from a peripheral nervous system deficit, such as a congenital nerve deficit or a nerve deficit due to trauma or an iatrogenic event. Alternatively, the peripheral nerve deficit may be due to infection or to autoimmune disease. The subject may suffer from a central nervous system deficit, such as where the nerve deficit is in the brain or spinal cord. The peripheral nerve deficit may be a nerve deficit in a cranial nerve or a spinal nerve. The spinal nerve deficit may be congenital or due to trauma or an iatrogenic event. The spinal nerve deficit may be due to infection or to autoimmune disease. The spinal nerve deficit may be a cervical deficit, a lumbosacral deficit, or a thoracic deficit. The subject may a non-human animal, such as a bird, a reptile or a mammal. The subject may be a human.

The method may further comprise treating said subject with physical therapy or other nerve deficit therapy prior to, at the time of, or post-administration. The administering results in improved sensory function in said subject, such as nociceptive function and/or mechanoceptive function. The administering may result in improved motor control in said subject, such as fine motor control, gross motor control or autonomic nerve control.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the disclosure, and vice versa. Furthermore, compositions and kits of the disclosure can be used to achieve methods of the disclosure.

Throughout this application, the term "about" is used to indicate that a value includes the inherent variation of error for the device, the method being employed to determine the value, or the variation that exists among the study subjects.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device or a method that "comprises," "has," "contains," or "includes" one or more elements possesses those one or more elements but is not limited to possessing only those one or more elements or steps. Likewise, an element of a device or method that "comprises," "has," "contains," or "includes" one or more features possesses those one or more features but is not limited to possessing only those one or more features.

DESCRIPTION OF ILLUSTRATIVE EMBODIMENTS

Nerve deficits and injuries constitute a major challenge for health care providers and represent a tremendous financial strain on insurance companies as well as individuals suffering from such injuries. One significant example is spinal cord injury (SCI), which commonly results in permanent paralysis and sensory impairments due to poor spontaneous nerve regeneration in the central nervous system. This is even more exacerbated when the injury results in tissue loss as a consequence of trauma. This normally follows by cell death at the injury epicenter, which forms a fluid filled cyst that prevents axonal regeneration.

Another significant example is nerve injury in the upper and lower extremities, which also results in permanent paralysis and sensory impairments due to poor spontaneous nerve regeneration in the peripheral nervous system. Even when a nerve is cut and directly repaired, the recovery is suboptimal and represents only a fraction of the pre-injury function. This is even more exacerbated when the injury results in tissue loss as a consequence of trauma. The nerve has no potential for spontaneous regeneration across this nerve tissue defect, or nerve gap.

A number of strategies have been proposed to repair injured nerve tissue such as nerve gaps, including scaffolds and hollow conduits made of degradable or nondegradable materials such as PLGA, PGE, multiluminal agarose hydrogels, or silicone; and exogenous growth factors, matrix molecules, or cells (e.g., recombinant cells) to deliver molecules that entice nerve regeneration. Surgical implantation of scaffolds or hollow conduits alone permits regeneration across nerve gaps of 1-3 cm, but use of exogenous cells, or exogenous molecules plus scaffolds, are required for regeneration across larger nerve gaps, known as critical gaps. Here, the inventors identified a new type of therapeutic approach to addressing nerve deficits. Using immunodulatory compounds, and in particular a cocktail of different classes of immunodulatory compounds including CXCR4 antagonists, STAT3 activators and NO-increasing agents, the inventors have been able to achieve nerve regeneration across an empty critical gap of >3 cm in length.

The existing paradigms for treating nerve gaps using scaffolds or hollow conduits typically fail to bridge the critical gap, which is the highest barrier in nerve regeneration and previously impossible to overcome without exogenous cells, or exogenous molecules plus scaffolds. Distances less than the critical gap can be easily overcome even in the absence of exogenous cells or molecules. In contrast, the inventors have shown that the use of single or combinatorial immunodulatory drug treatments induces whole tissue nerve regeneration across distances greater than the critical gap and can do so without the addition of scaffolds or exogenous cells.

These and other aspects of the disclosure are described in detail below.

1. Nerve Injuries and Defects

Nerve injury, broadly defined, is injury to nervous tissue. There is no single classification system that can describe all the many variations of nerve injury. In 1941, Seddon introduced a classification of nerve injuries based on three main types of nerve fiber injury and whether there is continuity of the nerve. Usually, however, (peripheral) nerve injury is classified in five stages, based on the extent of damage to both the nerve and the surrounding connective tissue, since supporting glial cells may be involved. Unlike in the central nervous system, neuroregeneration in the peripheral nervous system is possible. The processes that occur in peripheral regeneration can be divided into the following major events: Wallerian degeneration, axon regeneration/growth, and end-organ reinnervation. The events that occur in peripheral regeneration occur with respect to the axis of the nerve injury. The proximal stump refers to the end of the injured neuron that is still attached to the neuron cell body; it is the part that regenerates. The distal stump refers to the end of the injured neuron that is still attached to the end of the axon; it is the part of the neuron that will degenerate but that remains in the area toward which the regenerating axon grows.

Neuropraxia is the least severe form of nerve injury, with complete recovery. In this case, the axon remains intact, but there is myelin damage causing an interruption in conduction of the impulse down the nerve fiber. Most commonly, this involves compression of the nerve or disruption to the blood supply (ischemia). There is a temporary loss of function which is reversible within hours to months of the injury (the average is 6-9 weeks). Wallerian degeneration does not occur, so recovery does not involve actual regeneration. In electrodiagnostic testing with nerve conduction studies, there is a normal compound motor action potential amplitude distal to the lesion at day 10, and this indicates a diagnosis of mild neuropraxia instead of axonotmesis or neurotmesis.

Axonotmesis a more severe nerve injury with disruption of the neuronal axon, but with maintenance of the epineurium. This type of nerve damage may cause loss of the motor, sensory, and autonomic functions. This is mainly seen in crush injury.

If the force creating the nerve damage is removed in a timely fashion and the surrounding tissue is preserved, the axon may regenerate, leading to recovery. Electrically, the nerve shows rapid and complete degeneration, with loss of voluntary motor units. Regeneration of the motor end plates will occur, as long as the endoneural tubules are intact.

Axonotmesis involves the interruption of the axon and its covering of myelin but preservation of the connective tissue framework of the nerve (the encapsulating tissue, the epineurium and perineurium, are preserved). Because axonal continuity is lost, Wallerian degeneration occurs. Electromyography (EMG) performed 2 to 4 weeks later shows fibrillations and denervation potentials in musculature distal to the injury site. Loss in both motor and sensory spines is more complete with axonotmesis than with neurapraxia, and recovery occurs only through regenerations of the axons, a process requiring time.

Axonotmesis is usually the result of a more severe crush or contusion than neuropraxia but can also occur when the nerve is stretched (without damage to the epineurium). There is usually an element of retrograde proximal degeneration of the axon, and for regeneration to occur, this loss must first be overcome. The regenerating fibers must cross the injury site and regeneration through the proximal or retrograde area of degeneration may require several weeks. Then the neurite tips progress down to the distal site, such as the wrist or hand. Proximal lesion may grow distally as fast as 2 to 3 mm per day and distal lesion as slowly as 1.5 mm per day. Regeneration occurs over weeks to years.

Neurotmesis is the most severe lesion with no potential of full recovery. It occurs on severe contusion, stretch, laceration, or local anesthetic toxicity. The axon and encapsulating connective tissue lose their continuity. The last (extreme) degree of neurotmesis is transection, but most neurotmetic injuries do not produce gross loss of continuity of the nerve but rather internal disruption of the architecture of the nerve sufficient to involve perineurium and endoneurium as well as axons and their covering. Denervation changes recorded by EMG are the same as those seen with axonotmetic injury. There is a complete loss of motor, sensory and autonomic function. If the nerve has been completely divided, axonal regeneration causes a neuroma to form in the proximal stump. For neurotmesis, it is better to use a new more complete classification called the Sunderland System.

The following are exemplary nerve defects that can be addressed by the appoach outlined in the present disclosure.

A. Spinal Cord Nerve Defects

A spinal cord injury (SCI) or defect is an injury to the spinal cord resulting in a disruption, either temporary or permanent, in the cord's normal motor, sensory, or autonomic function. Common causes of damage are trauma (car accident, gunshot, falls, sports injuries, etc.) or disease (transverse myelitis, polio, spina bifida, Friedreich's ataxia, etc.). The spinal cord does not have to be severed in order for a loss of function to occur. Depending on where the spinal cord and nerve roots are damaged, the symptoms can vary widely, from pain to paralysis to incontinence. Spinal cord injuries are described at various levels of "incomplete," which can vary from having no effect on the patient to a "complete" injury which means a total loss of function.

Treatment of spinal cord injuries starts with restraining the spine and controlling inflammation to prevent further damage. The actual treatment can vary widely depending on the location and extent of the injury. In many cases, spinal cord injuries require substantial physical therapy and rehabilitation, especially if the patient's injury interferes with activities of daily life.

Research into treatments for spinal cord injuries includes nerve regeneration through the use of nerve growth factors, controlled hypothermia and stem cells, though many treatments have not been studied thoroughly and very little new research has been implemented in standard care.

B. Brain Injury and Cranial Nerve Deficits

Brain damage or brain injury (BI) is the destruction or degeneration of brain cells, including nerves. Brain injuries occur due to a wide range of internal and external factors. A common category with the greatest number of injuries is traumatic brain injury (TBI) following physical trauma or head injury from an outside source, and the term acquired brain injury (ABI) is used in appropriate circles to differentiate brain injuries occurring after birth from injury due to a disorder or congenital malady.[1]

In general, brain damage refers to significant, undiscriminating trauma-induced damage, while neurotoxicity typically refers to selective, chemically induced neuron damage. Brain injuries occur due to a very wide range of conditions, illnesses, injuries, and as a result of iatrogenesis (adverse effects of medical treatment). Possible causes of widespread brain damage include birth hypoxia, prolonged hypoxia (shortage of oxygen), poisoning by teratogens (including alcohol), infection, and neurological illness. Chemotherapy can cause brain damage to the neural stem cells and oligodendrocyte cells that produce myelin. Common causes of focal or localized brain damage are physical trauma (traumatic brain injury, stroke, aneurysm, surgery, other neurological disorder), and poisoning from heavy metals including mercury and compounds of lead.

Cranial nerve disease is an impaired functioning of one of the twelve cranial nerves. It is possible for a disorder of more than one cranial nerve to occur at the same time, if a trauma occurs at a location where many cranial nerves run together, such as the jugular fossa. A brainstem lesion could also cause impaired functioning of multiple cranial nerves, but this condition would likely also be accompanied by distal motor impairment.

The facial nerve is the seventh of 12 cranial nerves. This cranial nerve controls the muscles in the face. Facial nerve palsy is more abundant in older adults than in children and is said to affect 15-40 out of 100,000 people per year. This disease comes in many forms which include congenital, infectious, traumatic, neoplastic, or idiopathic. The most common cause of this cranial nerve damage is Bell's palsy (idiopathic facial palsy) which is a paralysis of the facial nerve. Although Bell's palsy is more prominent in adults it seems to be found in those younger than 20 or older than 60 years of age. Bell's palsy is thought to occur by an infection of the herpes virus which may cause demyelination and has been found in patients with facial nerve palsy. Symptoms include flattening of the forehead, sagging of the eyebrow, and difficulty closing the eye and the mouth on the side of the face that is affected. The inability to close the mouth causes problems in feeding and speech. It also causes lack of taste, lacrimation, and sialorrhea.

C. Peripheral Nerve Deficits

Peripheral nerve damage is categorized in the Seddon classification based on the extent of damage to both the nerve and the surrounding connective tissue since the nervous system is characterized by the dependence of neurons on their supporting glia. Unlike in the central nervous system, regeneration in the peripheral nervous system is possible. The processes that occur in peripheral regeneration can be divided into the following major events: Wallerian degeneration, axon regeneration/growth, and end-organ reinnervation. The events that occur in peripheral regeneration occur with respect to the axis of the nerve injury. The proximal stump refers to the end of the injured neuron that is still attached to the neuron cell body; it is the part that regenerates. The distal stump refers to the end of the injured neuron that is still attached to the end of the axon; it is the part that will degenerate but remains the area that the regenerating axon grows toward.

The lowest degree of nerve injury in which the nerve remains intact but its signaling ability is damaged is called neurapraxia. The second degree in which the axon is damaged, but the surrounding connecting tissue remains intact is called axonotmesis. The last degree in which both the axon and connective tissue are damaged is called neurotmesis.

2. Immunomodulatory Drugs

As discussed above, the present inventors have determined that CXCR4 antagonists, STAT3 activators, and NO-increasing agentsall function to promote nerve growth and regeneration. Therefore, they contemplate the use of the agents invidually or in combination for treating a wide variety of nerve deficits.

A. CXCR4 Antagonists

C-X-C chemokine receptor type 4 (CXCR-4) also known as fusin or CD184 (cluster of differentiation 184) is a protein that in humans is encoded by the CXCR4 gene. CXCR-4 is an alpha-chemokine receptor specific for stromal-derived-factor-1 (SDF-1 also called CXCL12), a molecule endowed with potent chemotactic activity for lymphocytes. CXCR4 is one of several chemokine receptors that HIV can use to infect CD4+ T cells. HIV isolates that use CXCR4 are traditionally known as T-cell tropic isolates. Typically, these viruses are found late in infection. It is unclear as to whether the emergence of CXCR4-using HIV is a consequence or a cause of immunodeficiency.

CXCR4 is upregulated during the implantation window in natural and hormone replacement therapy cycles in the endometrium, producing, in presence of a human blastocyst, a surface polarization of the CXCR4 receptors suggesting that this receptor is implicated in the adhesion phase of human implantation.

CXCR4's ligand SDF-1 is known to be important in hematopoietic stem cell homing to the bone marrow and in hematopoietic stem cell quiescence. It has been also shown that CXCR4 signalling regulates the expression of CD20 on B cells. Until recently, SDF-1 and CXCR4 were believed to be a relatively monogamous ligand-receptor pair (other chemokines are promiscuous, tending to use several different chemokine receptors). Recent evidence demonstrates ubiquitin is also a natural ligand of CXCR4. Ubiquitin is a small (76-amino acid) protein highly conserved among eukaryotic cells. It is best known for its intracellular role in targeting ubiquitylated proteins for degradation via the ubiquitin proteasome system. Evidence in numerous animal models suggests ubiquitin is anti-inflammatory immune modulator and endogenous opponent of proinflammatory damage associated molecular pattern molecules. It is speculated this interaction may be through CXCR4 mediated signalling pathways. MIF is an additional ligand of CXCR4.

CXCR4 is present in newly generated neurons during embryogenesis and adult life where it plays a role in neuronal guidance. The levels of the receptor decrease as neurons mature. CXCR4 mutant mice have aberrant neuronal distribution. This has been implicated in disorders such as epilepsy.

Drugs that block the CXCR4 receptor appear to be capable of "mobilizing" hematopoietic stem cells into the bloodstream as peripheral blood stem cells. Peripheral blood stem cell mobilization is very important in hematopoietic stem cell transplantation (as a recent alternative to transplantation of surgically harvested bone marrow) and is currently performed using drugs such as G-CSF. G-CSF is a growth factor for neutrophils (a common type of white blood cells) and may act by increasing the activity of neutrophil-derived proteases such as neutrophil elastase in the bone marrow leading to proteolytic degradation of SDF-1. Plerixafor (AMD3100) is a drug, approved for routine clinical use, which directly blocks the CXCR4 receptor. It is a very efficient inducer of hematopoietic stem cell mobilization in animal and human studies. In a small human clinical trial to evaluate the safety and efficacy of fucoidan ingestion (brown seaweed extract), 3 g daily of 75% w/w oral fucoidan for 12 days increased the proportion of CD34+CXCR4+ from 45 to 90% and the serum SDF-1 levels, which could be useful in CD34+ cells homing/mobilization via SDF-1/CXCR4 axis.

It has been associated with WHIM syndrome. WHIM like mutations in CXCR4 were recently identified in patients with Waldenstrom's macroglobulinemia, a B-cell malignancy. The presence of CXCR4 WHIM mutations has been associated with clinical resistance to ibrutinib in patients with Waldenstrom's Macroglobulinemia.

While CXCR4's expression is low or absent in many healthy tissues, it was demonstrated to be expressed in over 23 types of cancer, including breast cancer, ovarian cancer, melanoma, and prostate cancer. Expression of this receptor in cancer cells has been linked to metastasis to tissues containing a high concentration of CXCL12, such as lungs, liver and bone marrow. However, in breast cancer where SDF1/CXCL12 is also expressed by the cancer cells themselves along with CXCR4, CXCL12 expression is positively correlated with disease free (metastasis free) survival. CXCL12 (over-)expressing cancers might not sense the CXCL12 gradient released from the metastasis target tissues since the receptor, CXCR4, is saturated with the ligand produced in an autocrine manner. Another explanation of this observation is provided by a study that shows the ability of CXCL12 (and CCL2) producing tumors to entrain neutrophils that inhibit seeding of tumor cells in the lung.

Chronic exposure to THC has been shown to increase T lymphocyte CXCR4 expression on both CD4+ and CD8+T lymphocytes in rhesus macaques. It has been shown that BCR signalling inhibitors also affect CXCR4 pathway and thus CD20 expression. CXCR4 has been shown to interact with USP14.

A CXCR4 antagonist is a substance which blocks the CXCR4 receptor and prevents its activation. Blocking the receptor stops the receptor's ligand, CXCL12, from binding which prevents downstream effects. CXCR4 antagonists are especially in important for hindering cancer progression because one of the downstream effects initiated by CXCR4 receptor activation is cell movement which helps the spread of cancer, known as metastasis. The CXCR4 receptor has been targeted by antagonistic substances since being identified as a co-receptor in HIV and assisting the development of cancer. Macrocyclic ligands have been utilised as CXCR4 antagonists.

Plerixafor is an example of a CXCR4 antagonist, and has approvals (e.g., U.S. FDA 2008) for clinical use (to mobilize hematopoietic stem cells). BL-8040 is a CXCR4 antagonist that has undergone clinical trials (e.g., in various leukemias), with one planned for pancreatic cancer (in combination with pembrolizumab). Previously called BKT140, it is a synthetic cyclic 14-residue peptide with an aromatic ring. In a 2018 mouse tumor model study, BL-8040 treatment enhanced anti-tumor immune response potentially by increasing the $CD8^+$ T-cells in the tumor microenvironment.

WZ 811, an agent with a different molecular structure from Plerixafor, has also been used.

B. STAT3 Activators

Signal transducer and activator of transcription 3 (STAT3) is a transcription factor which in humans is encoded by the STAT3 gene. It is a member of the STAT protein family.

STAT3 is a member of the STAT protein family. In response to cytokines and growth factors, STAT3 is phosphorylated by receptor-associated Janus kinases (JAK), form homo- or heterodimers, and translocate to the cell nucleus where they act as transcription activators. Specifically, STAT3 becomes activated after phosphorylation of tyrosine 705 in response to such ligands as interferons, epidermal growth factor (EGF), Interleukin (IL-)5 and IL-6. Additionally, activation of STAT3 may occur via phosphorylation of serine 727 by Mitogen-activated protein kinases (MAPK) and through c-src non-receptor tyrosine kinase. STAT3 mediates the expression of a variety of genes in response to cell stimuli, and thus plays a key role in many cellular processes such as cell growth and apoptosis.

STAT3-deficient mouse embryos cannot develop beyond embryonic day 7, when gastrulation begins. It appears that at these early stages of development, STAT3 activation is required for self-renewal of embryonic stem cells (ESCs). Indeed, LIF, which is supplied to murine ESC cultures to maintain their undifferentiated state, can be omitted if STAT3 is activated through some other means.

STAT3 is essential for the differentiation of the TH17 helper T cells, which have been implicated in a variety of autoimmune diseases. During viral infection, mice lacking STAT3 in T-cells display impairment in the ability to generate T-follicular helper (Tfh) cells and fail to maintain antibody-based immunity.

Loss-of-function mutations in the STAT3 gene result in Hyperimmunoglobulin E syndrome, associated with recurrent infections as well as disordered bone and tooth development. Gain-of-function mutations in the STAT3 gene have been reported to cause multi-organ early onset auto-immune diseases; such as thyroid disease, diabetes, intestinal inflammation, and low blood counts, while constitutive STAT3 activation is associated with various human cancers and commonly suggests poor prognosis. It has anti-apoptotic as well as proliferative effects.

STAT3 can promote oncogenesis by being constitutively active through various pathways as mentioned elsewhere. A tumor suppressor role of STAT3 has also been reported. In the report on human glioblastoma tumor, or brain cancer, STAT3 was shown to have an oncogenic or a tumor suppressor role depending upon the mutational background of the tumor. A direct connection between the PTEN-Akt-FOXO axis (suppressive) and the leukemia inhibitory factor receptor beta (LIFRbeta)-STAT3 signaling pathway (oncogenic) was shown.

Increased activity of STAT3 in cancer cells, leads to changes in the function of protein complexes that control expression of inflammatory genes, with result profound change in the secretome and the cell phenotypes, their activity in the tumor, and their capacity for metastasis. Niclosamide seems to inhibit the STAT3 signalling pathway.

STAT3 has been shown to interact with AR, ELP2, EP300, EGFR, HIF1A, JAK1, JUN, KHDRBS1, mTOR, MYOD1, NDUFA13, NFKB1, NR3C1, NCOA1, PML, RAC1, RELA, RET, RPA2, STAT1, Stathmin, Src, TRIP10 and KPNA4.

STAT3 activators include colivelin, and neuroprotective peptide, ruxolitinib phosphate, a JAK1/JAK2 inhibitor, or IL-6.

C. NO Promoting Agents

Nitric oxide (nitrogen oxide or nitrogen monoxide) is a colorless gas with the formula NO. It is one of the principal oxides of nitrogen. Nitric oxide is a free radical, i.e., it has an unpaired electron, which is sometimes denoted by a dot in its chemical formula, i.e., NO. Nitric oxide is also a heteronuclear diatomic molecule, a historic class that drew researches which spawned early modern theories of chemical bonding. An important intermediate in chemical industry, nitric oxide forms in combustion systems and can be generated by lightning in thunderstorms. In mammals, including humans, nitric oxide is a signaling molecule in many physiological and pathological processes. Nitric oxide should not be confused with nitrous oxide ($N_2O$), an anesthetic, or with nitrogen dioxide ($NO_2$), a brown toxic gas and a major air pollutant.

NO promotingNO donors include (+/−)-S-Nitroso-N-acetylpenicillamine, Molsidomine, 3-Morpholinosydnonimine, Hydroxyguanidine sulfate, Tetrahydrobiopterin (THB) dihydrochloride, S-Nitrosoglutathione (GSNO), Streptozotocin (U-9889), Nicorandil, Dephostatin, DETA NONOate, NOC-12, NOC-18, NOC-5, NOC-7, MAHMA NONOate, PAPA NONOate, Sulfo-NONOate disodium salt, Angeliprimes salt, Diethylamine NONOate, NOR-1, NOR-2, NOR-3, NOR-4, Spermine NONOate, beta-Gal NONOate, BNN3, GEA 3162, GEA 5024, Sodium nitroprusside dihydrate, 10-Nitrooleate, BEC, NO-Indomethacin, Pilotyprimes Acid, SE 175, V-PYRRO/NO, Vinyl-L-NIO Hydrochloride, AMI-1, sodium salt, DAF-FM DA (cell permeable), GEA 5583, N-Acetyl-D,L-penicillamine disulfide, SIN-IA/gammaCD Complex, 4-Phenyl-3-furoxancarbonitrile, JS-K, Lansoprazole Sulfone N-Oxide, NO-Aspirin 1, Glyco-SNAP-2, N,N-Dicarboxymethyl-N,N-dinitroso-p-phenylenediamine (Disodium Salt), (2S)-(+)-Amino-6-iodo-acetamidohexanoic acid, 4AF DA, BEC ammonium salt, DAF-2 DA (cell permeable), DAN-1 EE hydrochloride, DD1, DD2, Diethylamine NONOate/AM, Fructose-SNAP-1, Glyco-SNAP-1, Guanylyl Cyclase, Hydroxyguanidine hemisulfate, N-Cyclopropyl-N'-hydroxyguanidine hydrochloride, NOR-5, PROLI NONOate, S-Nitrosocaptopril, 4-(p-methoxyphenyl)-1,3,2-Oxathiazolylium-5-olate, 4-chloro-4-phenyl-1,3,2-Oxathiozolylium-5-olate, 4-phenyl-1,3,2-Oxathiazolylium-5-olate, 4-trifluoro-4-phenyl-1, 3,2-Oxathiazolylium-5-olate, Tricarbonyldichlororuthenium (II) dimer, DL-alpha-Difluoromethylornithine hydrochloride, Geranylgeranylacetone, N-Nitrosodiethylamine, L-NMMA (citrate), and 3-(Methylnitrosamino)propionitrile. SIN-1 chloride, L-Arginine, SNAP have also been used in experiments.

Other drug classes can also serve to increase local concentrations of nitric oxide, such as PDE5 inhibitors (e.g., sildenafil). Another NO-promoting agent is L-arginine, which is a substrate for NO synthase.

D. Pharmaceutical Formulations and Methods of Administration.

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

The active compositions of the present invention may include classic pharmaceutical preparations. One will generally desire to employ appropriate salts and buffers to render agents stable and allow for uptake by target cells. Aqueous compositions of the present invention comprise an effective amount of the agent(s) to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the present invention, its use in therapeutic compositions is contemplated. Supplementary active ingredients also can be incorporated into the compositions.

Administration of these compositions according to the present invention will be via an appropriate route but are particularly drawn to administration local or regional to a nerve deficit. Administration may be by injection or infusion. Such compositions would normally be administered as pharmaceutically acceptable compositions. When the route is topical, the form may be a cream, ointment, or salve.

An effective amount of the therapeutic agent is determined based on the intended goal, i.e., improving nerve growth, reducing a nerve deficit, and/or bridging a "critical gap." The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

As used herein, the term in vitro preparation refers to manipulations performed on materials outside of the living animal. The term ex vivo administration refers to materials that have been manipulated in vitro and are subsequently administered to a living animal. The term in vivo administration includes all manipulations performed within an animal. In certain aspects of the present invention, the compositions may be prepared in vitro or administered either ex vivo or in vivo.

In the case of surgical intervention, the present invention may be used preoperatively, during surgery, or post-operatively. The administration may be continued post-surgery, for example, by leaving a catheter implanted at the site of the surgery. Periodic post-surgical treatment also is envisioned. Generally, the dose of the therapeutic composition via continuous perfusion will be equivalent to that given by single or multiple injections, adjusted over a period of time during which the perfusion occurs.

Treatment regimens may vary as well, and often depend on deficit type, deficit location, and health and age of the patient. Obviously, certain types of deficits will require more aggressive treatment, while at the same time, certain patients cannot tolerate more taxing protocols. The clinician will be best suited to make such decisions based on the known efficacy and toxicity (if any) of the therapeutic formulations.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are dimethyl sulfoxide, propylene glycol, polyethylene glycol, vegetable oil and injectable organic esters such as ethyloleate. Aqueous carriers include water, alcoholic/aqueous solutions, saline solutions, parenteral vehicles such as sodium chloride or Ringer's dextrose. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

E. Combination Therapy

The inventors have determined that combinations of the aforementioned agents, pairwise combinations, or a triple combination, are particularly efficacious in addressing nerve deficits and promoting nerve growth and regeneration. These compositions would be provided in a combined amount effective to accomplish any or all of the foregoing goals. This process may involve providing agent(s) or factor(s) to a cell, tissue or subject at the same time. This may be achieved by treating the cell, tissue, or subject with one or more compositions or pharmacological formulation that include two or three agents, or by treating the cell, tissue, or subject with one, two or three distinct compositions or formulations.

Alternatively, the various agents may precede or follow the second (and/or third) agent or treatment by intervals ranging from minutes to weeks. In embodiments where the second agent (and/or third) and the first agent are administered separately, one would generally ensure that a significant period of time did not expire between the time of each delivery, such that the second (and/or third) agent and the first would still be able to exert an advantageously combined effect on the cell, tissue, or subject. In such instances, it is contemplated that one would treat the cell, tissue, or subject with multiple modalities within about 12-24 hr of each other and, more preferably, within about 6-12 hr of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. It also is conceivable that more than one administration of the first and/or the second and/or the third agent will be desired.

3. Nerve Growth Support Structures and Other Nerve Promoting Agents

In certain embodiments, the inventors contemplate inserting supports into the site of nerve deficits in order to provide a substrate upon and/or through which nerves may regrow. The support structures may be combined with other features, such as bioactive materials that are positioned within or adjacent to the support structure, as well as various biological factors that may stimulate, promote or improve nerve growth.

A. Conduits

Conduits are defined by elongated tubular structures with open ends and a lumen passing therethrough. While the exemplified conduits have a circular cross-section, they may be other shapes as well, such as oval, square, rectangular or hexagonal. The conduits maybe rigid to semi-rigid in nature, sustaining a force of 100 kPa to 2.0 GPa. They may be non-biodegradable, or at least not biodegradable for months to years following implantation.

The conduits may be formed from poly-lactide acid, polyurethane, silicone, cellulose, collagen, poly-lactide co-glycolic acid, polycaprolactone or processed natural extracellular matrix. The conduits may be from about 0.5 mm to about 6 cm or greater in length, from about 1.5 mm to about 4.0 mm in external diameter, with a lumen from about 1.5 mm to about 3.0 mm diameter. The conduit wall may be about 0.2 mm to about 0.6 mm in thickness. The conduits may further be coated with bioactive materials or nerve growth enhancing agents, as discussed below. For example, collagen and other extracellular matrix components are contemplated as materials to coat the conduits.

B. Polymer Fibers

In another embodiment, the structure will be composed of polymer fibers that act as a regenerative guide for growing/regrowing nerve tissue. The fibers will act as a more traditional scaffold, with nerves growing on top or around the guide. Suitable polymers include poly-lactide acid, polyurethane, silicone, cellulose, collagen, poly-lactide co-glycolic acid, and polycaprolactone.

C. Bioactive Materials

In certain embodiments, the support structure may be surrounded or partially surrounded by bioactive materials; and/or the support structure may contain bioactive luminal fillers if it has hollow regions. This bioactive material is solid, semi-solid or gel that can provide further support for the growth of nerve tissue, as well as a depot for the delivery of growth enhancing agents (discussed below). Suitable substances for the bioactive material include agar, collagen, laminin, fibronectin, or glycoproteins.

The bioactive material can be of uniform nature or can be made to contain a differential concentration of molecules such as collagen, laminin, fibronectin, growth factors, biopolymers, and pharmacological agents. The bioactive material may be solid, or may contain micro-/nanoparticles, microcompartments or microchannels, again to facilitate growth of new nerve tissue through the conduit, and to act as a repository for agents.

The microcompartments in the lumen can be in turn filled with collagen, polymeric micro-/nanoparticles or fibers and/or cells such as Schwann cells, fibroblasts, immune cells, neurons, stem cells, induced ploripotential cells (IPCs), other autogenous cells, and/or other exogenous cells. These cells can be genetically modified to enhance nerve regeneration such as by expressing growth factors or surface molecules.

The microcompartments can be used also to provide a controlled environment for the cells cultured in it prior to implantation or those migrating into it after implantation. This environment can consist in incorporating diverse means for the sustained delivery of growth factors, cytokines, anti-inflammatory, and other growth enhancing molecules.

Among the growth enhancing molecules incorporated into the structural support can be blockers for growth inhibitory molecules including those designed to block myelin-associated inhibitors (MAG and EphB3), and the chondroitin sulphate proteoglycans (CSPG) versican and neurocan.

D. Nerve Growth Factors

In certain embodiments, the bioactive materials may be desiged to deliver a growth factor. Alternatively, the structural support itself may be coated with a growth factor. These factors may be neurotrophic (NGF, BDNF, NT-3), glial-derived (GDNF) or pleotropic (PTN, VEGF).

Nerve growth factor (NGF) is a small secreted protein that is important for the growth, maintenance, and survival of certain target neurons (nerve cells). It also functions as a signaling molecule. It is perhaps the prototypical growth factor, in that it is one of the first to be described. While "nerve growth factor" refers to a single factor, "nerve growth factors" refer to a family of factors also known as neurotrophins.

Members of the neurotrophin family well recognized for their growth promoting effect include Nerve Growth Factor (NGF), Brain-Derived Neurotrophic Factor (BDNF), Neurotrophin-3 (NT-3), and Neurotrophin 4/5 (NT-4/5). BDNF is a protein that is encoded by the BDNF gene. BDNF binds at least two receptors on the surface of cells that are capable of responding to this growth factor, TrkB and the LNGFR (low-affinity nerve growth factor receptor, also known as p75). It may also modulate the activity of various neurotransmitter receptors, including the Alpha-7 nicotinic receptor. BDNF has also been shown to interact with the reelin signaling chain.

Neurotrophin-3 is a protein that is encoded by the NTF3 gene. It has activity on certain neurons of the peripheral and central nervous system, helps to support the survival and differentiation of existing neurons, and encourages the growth and differentiation of new neurons and synapses. Neurotrophin-4 (NT-4), also known as neurotrophin-5 (NT-5) or NT-4/5, is encoded by the NTF4 gene. NT-4 is a neurotrophic factor that signals predominantly through the TrkB receptor tyrosine kinase.

The GDNF family of ligands (GFL) consists of four neurotrophic factors: glial cell line-derived neurotrophic factor (GDNF), neurturin (NRTN), artemin (ARTN), and persephin (PSPN). GFLs have been shown to play a role in a number of biological processes including cell survival, neurite outgrowth, cell differentiation and cell migration. In particular signalling by GDNF promotes the survival of dopaminergic neurons and potently promotes the survival of many types of neurons.

Pleiotrophin (PTN) also known as heparin-binding brain mitogen (HBBM) or heparin-binding growth factor 8 (HBGF-8), neurite growth-promoting factor 1 (NEGF1), heparin affinity regulatory peptide (HARP), or heparin binding growth associated molecule (HB-GAM), is encoded by the PTN gene. It is an 18-kDa growth factor that has a high affinity for heparin. It is structurally related to midkine and retinoic acid induced heparin-binding protein.

Vascular endothelial growth factor (VEGF), originally known as vascular permeability factor (VPF), is a signal protein produced by cells that stimulates vasculogenesis and angiogenesis. It is part of the system that restores the oxygen supply to tissues when blood circulation is inadequate. Serum concentration of VEGF is high in bronchial asthma and diabetes mellitus. VEGF's normal function is to create new blood vessels during embryonic development, new blood vessels after injury, muscle following exercise, and new vessels (collateral circulation) to bypass blocked vessels.

4. Examples

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute specifically contemplated modes for its practice. However, those of skill in the art should, in light of the present disclosure, appreciate that many changes can be made in the specific embodiments which are disclosed and still obtain a like or similar result without departing from the spirit and scope of the disclosure.

Example 1

A silicone tube is biologically inert and has been widely used for nerve regeneration studies (Lundborg et al., 1982b; Williams et al., 1983). Lundborg showed that the rat sciatic nerve never regenerates across an empty silicone tube when presented with a gap longer than 15 mm. We have shown in contrast that the rat sciatic nerve can regenerate across at least 30 mm in an empty silicone tube when treated with the invention disclosed herein. A 30 mm gap was selected since it is non-regenerative, and thus represents the most difficult nerve regeneration condition, and is conserved across all species (Strauch et al., 2001). Additionally, we have shown that the rat sciatic nerve can regenerate across a gap of at least 50 mm in an empty silicone tube when treated with the invention disclosed herein. Additionally, we have shown that the invention disclosed herein can also improve the outcomes in the simplest types of nerve injuries as represented by a sciatic nerve cut-and-immediate repair.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

5. REFERENCES

The following references, to the extent that they provide exemplary procedural or other details supplementary to those set forth herein, are specifically incorporated herein by reference.

PCT/US14/16905
U.S. Patent Publication No. 20070010831

What is claimed is:

1. A method of increasing nerve growth, regrowth or regeneration in a subject comprising administering to said subject a CXCR4 antagonist, a STAT3 activator, and/or an agent that increases nitric oxide content, wherein:
    (a) the CXCR4 antagonist is selected from the group consisting of Plerixafor, BL-8040, or WZ 811;
    (b) the STAT3 activator is selected from the group consisting of colivelin, neuroprotective peptide, ruxolitinib phosphate, a JAK1/JAK2 inhibitor, and IL-6, and
    (c) the agent that increases nitric oxide content is selected from the group consisting of (+/−)-S-Nitroso-N-acetyl-penicillamine, Molsidomine, 3-Morpholinosydnonimine, Hydroxyguanidine sulfate, Tetrahydrobiopterin (THB) dihydrochloride, S-Nitrosoglutathione (GSNO), Streptozotocin (U-9889), Nicorandil, Dephostatin, DETA NONOate, NOC-12, NOC-18, NOC-5, NOC-7, MAHMA NONOate, PAPA NONOate, Sulfo-NONOate disodium salt, Angeliprimes salt, Diethylamine NONOate, NOR-1, NOR-2, NOR-3, NOR-4, Spermine NONOate, beta-Gal NONOate, BNN3, GEA 3162, GEA 5024, Sodium nitroprusside dihydrate, 10-Nitrooleate, BEC, NO-Indomethacin, Pilotyprimes Acid, SE 175, V-PYRRO/NO, Vinyl-L-NIO Hydrochloride, AMI-1, sodium salt, DAF-FM DA (cell permeable), GEA 5583, N-Acetyl-D,L-penicillamine disulfide, SIN-1A/gammaCD Complex, 4-Phenyl-3-furoxancarbonitrile, JS-K, Lansoprazole Sulfone N-Oxide, NO-Aspirin 1, Glyco-SNAP-2, N,N-Dicarboxymethyl-N,N-dinitroso-p-phenylenediamine (Disodium Salt), (2S)-(+)-Amino-6-iodoacetamidohexanoic acid, 4AF DA, BEC ammonium salt, DAF-2 DA (cell permeable), DAN-1 EE hydrochloride, DD1, DD2, Diethylamine NONOate/AM, Fructose-SNAP-1, Glyco-SNAP-1, Guanylyl Cyclase, Hydroxyguanidine hemisulfate, N-Cyclopropyl-N'-hydroxyguanidine hydrochloride, NOR-5, PROLI NONOate, S-Nitroso-captopril, 4-(p-methoxyphenyl)-1,3,2-Oxathiazolylium-5-olate, 4-chloro-4-phenyl-1,3,2-Oxathiozolylium-5-olate, 4-phenyl-1,3,2-Oxathiazolylium-5-olate, 4-trifluoro-4-phenyl-1,3,2-Oxathiazolylium-5-olate, Tricarbonyldichloro-ruthenium (II) dimer, DL-alpha-Difluoromethylornithine hydrochloride, Geranylgeranylacetone, N-Nitrosodiethylamine, L-NMMA (citrate), and 3-(Methylnitrosamino)propionitrile, SIN-1 chloride, L-Arginine, SNAP, L-arginine and a PDE5 inhibitor wherein the method results in bridging of a critical gap of at least 3 cm.

2. The method of claim 1, wherein administering comprises administering a CXCR4 antagonist alone, a CXCR4 antagonist with a STAT3 activator, a CXCR4 antagonist with an agent that increases nitric oxide content, or a CXCR4 antagonist with a STAT3 activator and an agent that increases nitric oxide content.

3. The method of claim 1, further comprising inserting a physical support structure into the critical gap.

4. The method of claim 3, wherein said physical support structure is composed of poly-lactide acid, polyurethane, polydioxanone, silicone, cellulose, collagen, PLGA, polycaprolactone or processed natural extracellular matrix.

5. The method of claim 1, further comprising administering to said subject one or more nerve growth factors.

6. The method of claim 1, wherein said CXCR4 antagonist, said STAT3 activator, said agent that increases nitric oxide content and/or said one or more nerve growth factors are delivered in a time-dependent release fashion.

7. The method of claim 1, wherein no physical support structure is inserted into said subject.

8. The method of claim 1, wherein no growth factor is administered to said subject.

9. The method of claim 1, wherein the CXCR4 antagonist is administered prior to both the STAT3 activator or the agent that increases nitric oxide content, or the CXCR4 antagonist is administered after both the STAT3 activator or the agent that increases nitric oxide content, or the CXCR4 antagonist is administered between the STAT3 activator and the agent that increases nitric oxide content.

10. The method of claim 1, wherein the subject suffers from a peripheral nervous system deficit.

11. The method of claim 10, wherein said peripheral nerve deficit is congenital, due to trauma or an iatrogenic event, due to infection, or due to autoimmune disease.

12. The method of claim 1, wherein the subject suffers from a central nervous system deficit.

13. The method of claim 10, wherein the peripheral nerve deficit is a nerve deficit in a cranial nerve or a spinal nerve.

14. The method of claim 13, wherein said spinal nerve deficit is congenital, is due to trauma or an iatrogenic event, due to infection, due to autoimmune disease, a cervical deficit, a lumbosacral deficit, or a thoracic deficit.

15. The method of claim 1, wherein said subject is a non-human animal.

16. The method of claim 1, wherein said subject is a human.

17. The method of claim 1, further comprising treating said subject with physical therapy or other nerve deficit therapy prior to, at the time of, or post-administration.

18. The method of claim 1, wherein administering results in improved sensory function in said subject.

19. The method of claim 1, wherein administering results in improved motor control in said subject.

20. The method of claim 1, wherein said method results in bridging of a critical gap of 3.5 cm, 4 cm, 4.5 cm or 5 cm.

21. The method of claim 12, wherein the subject suffers from a nerve deficit in the brain or spinal cord.

* * * * *

UNITED STATES PATENT AND TRADEMARK OFFICE
CERTIFICATE OF CORRECTION

PATENT NO. : 11,969,522 B2
APPLICATION NO. : 16/922355
DATED : April 30, 2024
INVENTOR(S) : Keefer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 345 days.

Signed and Sealed this
Eighth Day of October, 2024

Katherine Kelly Vidal
*Director of the United States Patent and Trademark Office*